Figure 1A:
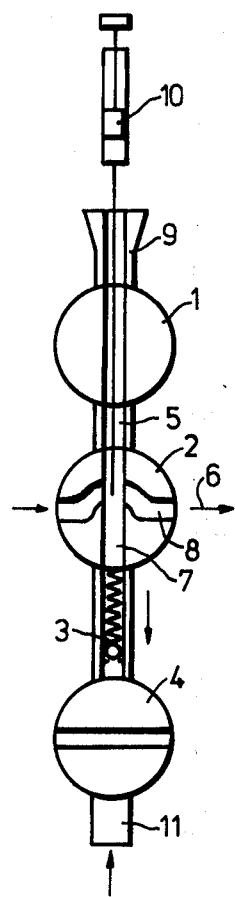

United States Patent [19]

Brandt et al.

[11] 4,165,644
[45] Aug. 28, 1979

[54] APPARATUS FOR INTRODUCING SAMPLES INTO HIGH PRESSURE GAS CHROMATOGRAPHS OR LIQUID CHROMATOGRAPHS

[75] Inventors: Hans-Walter Brandt, Unter-Odenthal; Günter Schnabel, Wermelskirchen; Karl-Heinz Müller, Bergisch-Gladbach, all of Fed. Rep. of Germany

[73] Assignee: Bayer Aktiengesellschaft, Leverkusen, Fed. Rep. of Germany

[21] Appl. No.: 890,733

[22] Filed: Mar. 27, 1978

[30] Foreign Application Priority Data

Apr. 9, 1977 [DE] Fed. Rep. of Germany ....... 2716013

[51] Int. Cl.² ............................................... G01N 1/10
[52] U.S. Cl. ............................................... 73/422 GC
[58] Field of Search ................................... 73/422 GC

[56] References Cited

U.S. PATENT DOCUMENTS 3,253,455  5/1966  Ferrin ........................... 73/422 GE
3,915,013  10/1975  Gaeke ........................... 73/422 GE Primary Examiner—S. Clement Swisher
Attorney, Agent, or Firm—Sprung, Felfe, Horn, Lynch & Kramer

[57] ABSTRACT

The combination of valves consists of a double passage cross-over spherical valve with which at least one other single passage spherical valve is connected in series. The passage of the cross-over spherical valve under high pressure is connected to the partition column of a gas chromatograph or liquid chromatograph while the other passage is intended for introducing the sample and is under atmospheric pressure when the sample is injected.

1 Claim, 7 Drawing Figures

APPARATUS FOR INTRODUCING SAMPLES INTO HIGH PRESSURE GAS CHROMATOGRAPHS OR LIQUID CHROMATOGRAPHS

The invention relates to a combination of valves for introducing samples into high pressure gas chromatographs or liquid chromatographs.

It is very difficult to introduce a mixture of substances reliably into the partition system of a high pressure gas chromatograph or liquid chromatograph. The substance is usually sluiced through a septum into the carrier gas or the carrier liquid (hereinafter referred to as the carrier fluid) by means of a syringe. As the carrier fluid is under a high pressure of the order of from 100 to 200 bar, it is difficult to obtain a seal to the exterior. Apart from this, it is absolutely impossible to introduce solid substances by this method.

The object of the invention is to provide a combination of valves for injecting gaseous, liquid or solid samples into a chromatograph dosing device at atmospheric pressure, using conventional syringes.

According to the invention there is provided an apparatus for introducing samples into a high-pressure gas liquid chromatograph, comprising a double passage crossover spherical valve which is connected in series with at least one single-passage spherical valve, and the passage of the cross-over spherical valve through which the carrier fluid flows under high pressure being connected to the partition column of a gas chromatograph or liquid chromatograph, while the other passage of the cross-over spherical valve is intended for introducing the sample and is under atmospheric pressure when the sample is injected. The sample is thus injected into the dosing device at atmospheric pressure in a first step and is sluiced into the carrier fluid under high pressure by rotating the double-passage spherical valve in a second step.

In an embodiment of the invention which is particularly suitable for high pressure gas chromatography the sample feed passage of the double-passage cross-over spherical valve communicates at one end via a single passage spherical valve with the atmosphere and is connected at the other end, via a check valve which opens at a pressure $P_L$ and closes after pressure compensation and another single-passage spherical valve, to the gas under high pressure for dissolving the sample substance. In this embodiment, the sample is injected without pressure into one channel of the double-passage cross-over spherical valve (solution chamber) in a first step. In the second step, the solution chamber is sealed from the atmosphere by means of a spherical cut-off valve, and the solution chamber temporarily communicates with the gas under high pressure for dissolving the sample substance. In the third and last step, the solution chamber is connected into the carrier gas channel by rotating the double-passage cross-over spherical valve.

The double-passage cross-over spherical valve has two separate flow channels in the spherical rotatable valve member, which are aligned with corresponding openings in the valve housing. The single-passage spherical valves, which merely serve as shut-off members in this case, only have one channel. Such valves are available as conventional components.

An advantage of the invention is that the samples may be injected at atmospheric pressure using a conventional syringe. It is not therefore necessary to use expensive high-pressure injection systems which are liable to break down. The problems of sealing encountered with high-pressure sluicing are avoided and it is possible to dispense with the septum formerly required. The combination of valves according to the invention is formed of conventional building components and may be built economically onto high-pressure partition systems.

Another substantial advantage is that the sample introduced is brought into contact with the gas (generally $CO_2$) provided for the solution at a higher pressure than that of the carrier gas. This improves the solubility of the sample substance in the solvent gas. The solvent gas, like the carrier gas, is in a super-critical condition at the high pressures used. When the solvent gas flows into the sample channel of the double-passage cross-over spherical valve (the solution chamber) the sample substance is additionally swirled in the solution chamber, thus ensuring a homogeneous distribution of the sample in the solution chamber.

The combination of valves according to the invention has the advantage that the quantity of sample sluiced into the partition system may be varied simply by rotating the double-passage cross-over spherical valve several times. A predetermined amount of sample is introduced into the partition system with each rotation. The total quantity of sample introduced is then determined by the number of rotations.

Figure 1B:
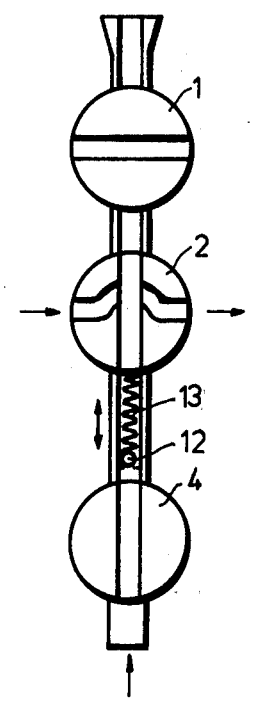
Figure 1C:
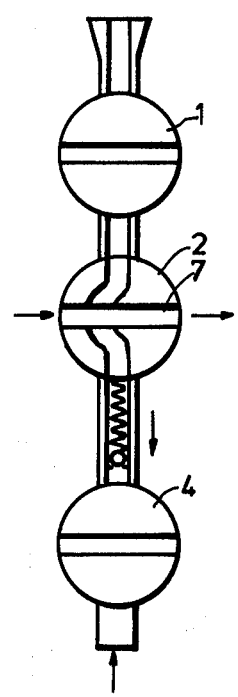
Figure 1D:
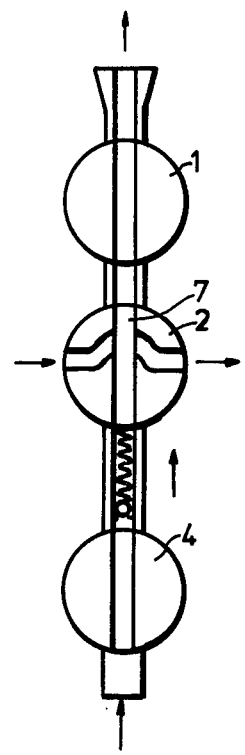
Figures 2A, 2B, 2C:
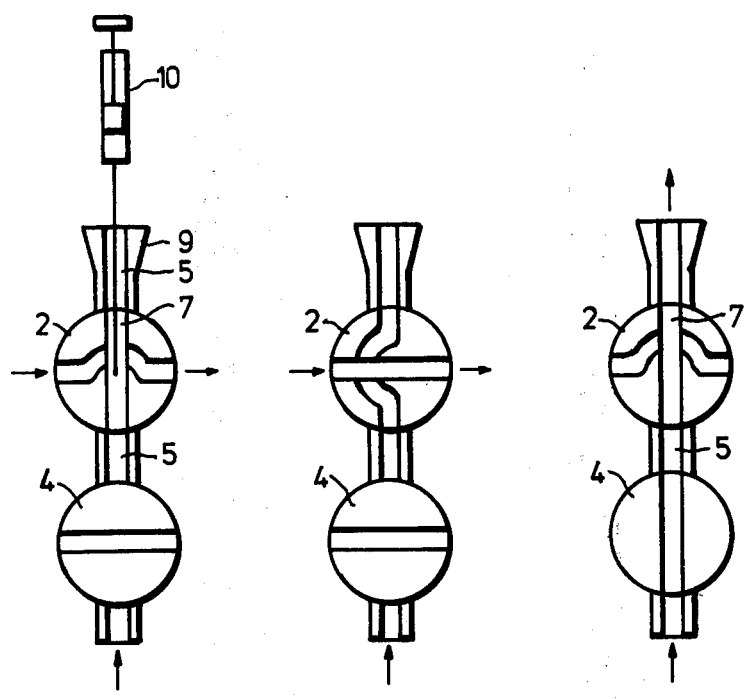

An embodiment of the invention is described in more detail below with reference to the accompanying drawings, in which FIGS. 1a to d show the various steps involved in sluicing a sample into a high-pressure gas chromatograph; and FIGS. 2a to c show the various steps involved in sluicing a sample into a liquid chromatograph.

The combination of valves shown in FIG. 1 consists of the spherical shut-off valve 1, a double-passage cross-over spherical valve 2, a check valve 3 and another spherical cut-off valve 4 which are arranged vertically above each other. A vertical channel defined by the valves 1 to 4 forms a sample feed passage 5. The channel marked by arrows at the level with the double-passage cross-over spherical valve 2 forms, a passage 6 for the carrier gas. The spherical valves 1, 2 and 4 each comprise of a spherical special steel valve body which is rotatable in a polytetrafluoraethylene housing. Such valves have a sufficient seal even at pressures of up to 200 bar and temperatures of up to 40° C. The valve body of the double-passage cross-over spherical valve 2 has two separate channels 7 and 8 which are perpendicular to each other. The upper end of the spherical cut-off valve 1 is provided with a sample feed nozzle 9. The valves are joined using conventional swage lock couplings (not shown).

In the position shown in FIG. 1a, a sample substance is injected by means of a syringe through the feed nozzle 9 into the channel 7, which acts as a solution chamber, of the double-passage cross-over valve 2. The left-hand of the other channel of the double-passage cross-over valve 2 is connected to a carrier gas source and the right-hand side is connected to the partition system of a gas chromatograph and carrier gas flows therethrough at pressures of between 50 and 120 bar and at a temperature of about 40° C. The spherical cut-off valve 1 thus communicates with the double-passage cross-over valve 2 in the injection position (FIG. 1a). The spherical cut-off valve 4 is closed. While the compressed carrier gas flows in the horizontal loop channel 6 at pressures of between 50 and 120 bar, the vertical sample feed passage 5 is not under pressure. The needle of the syringe is introduced into the solution chamber 7 of the double-passage cross-over valve to inject the gaseous, liquid or solid sample.

FIG. 1b shows the solution of the sample substance by a high-pressure gas. A $CO_2$ high-pressure gas reservoir at a pressure $P_L = 200$ bar is connected to the lower end 11 of the spherical cut-off valve 4 for this purpose. As shown in FIG. 1b, the valve 1 is closed and the valve 4 is opened. The $CO_2$ gas under high pressure now flows into the solution chamber 7 of the cross-over spherical valve 2 with the sample therein. The check valve 3 remains open until the pressure has been compensated. After pressure compensation, the ball 12 of the check valve is pressed back against the valve seat by the compression spring 13 and the solution chamber 7 is closed. The injection sample is swirled and homogeneously distributed in the solution chamber by the rapid inflex of the $CO_2$ gas therein. The high solution pressure of about 200 bar increases the solubility of the sample substance in the $CO_2$. As is known, $CO_2$ behaves like a liquid at temperatures of 31.5° C. and pressures of 200 bar. The introducing step shown in FIG. 1b would not be simply possible in a conventional injection apparatus since the pressure of the carrier gas must not generally exceed a maximum of 120 bar for gas chromatographic partition. Before the sample is introduced into the partition system, the sample substance should be in equilibrium with the $CO_2$ for about 2 minutes under a pressure of 200 bar.

The sample substance is sluiced in as shown in FIG. 1c. The cross-over spherical valve 2 is rotated through 90° and the spherical cut-off valve 4 is closed. The solution chamber 7 now extends horizontally and communicates the continuously flowing carrier gas. The dissolved sample is thus flushed into the subsequent partition system of the high-pressure gas chromatograph. The sample is either sluiced in by a single 90° rotation of the valve body or by several rotations. With the latter mode of operation, sluicing may be divided into several stages. Each rotation of the valve body causes a proportion of the sample dissolved in the channel 7 to be conveyed into the partition system.

It is necessary to cleanse the combination of valves after each sample is introduced. As shown in FIG. 1d the double-passage cross-over spherical valve is turned back into the starting position and the spherical cut-off valves 1 and 4 are opened for a short period so that the sample feed passage 5 is temporarily connected to the $CO_2$ gas source. The sample feed passage including the solution chamber 7 is flushed clean as a result of the high pressure.

FIG. 2 shows an embodiment of a combination of valves according to the invention for introducing samples into high-pressure liquid chromatographs. The sample is introduced at atmospheric pressure, as in FIG. 1.

The valve combination consists simply of a double-passage cross-over valve and a cut-off valve. The straight opening is formed conically. The conical arrangement is necessary to prevent the sample from admixing with the eluate when the sample is sluiced in. The vertical channel forms the sample feed passage 5 as in the first embodiment.

In the first step (FIG. 2a) the liquid to be examined is again sprayed into the conical section 7 of the cross-over spherical valve 2 using a conventional syringe 10. The sample is again introduced at atmospheric pressure.

The sample substance is sluiced into the partition system as shown in FIG. 2b. The valve body of the valve 2 is rotated through 90° so that the solution chamber 7 is aligned with the channel. The sample injected into the solution chamber 7 is thus brought into contact with the carrier liquid while the tapering section is always on the side of the column attachment. The column attachment should be continued in the diameter of the smallest conical opening.

The last step is flushing of the solution chamber 7, as shown in FIG. 2c. The valve 2 is turned back into the starting position and the spherical cut-off valve 4 is opened so that the sample feed passage is connected to a flushing gas source at a super-atmospheric pressure of about 2 bar. Nitrogen or air are suitable as the flushing gas. In this manner the sample feed passage 5 is cleared of residual solution through the connecting nozzles 9. The combination of valves is thus ready for the introducing the next sample.

What we claim is:

1. An apparatus for introducing samples into a high pressure fluid chromatograph having a partition column and a high pressure carrier fluid flow passage to the partition, comprising a double passage cross over spherical valve, two single-passage spherical valves connected in series therewith to define a sample passage, wherein one passage of the cross-over spherical valve is alignable with the carrier fluid passage to the partition column while the other passage of the cross-over spherical valve is aligned with the sample passage for introducing the sample under atmospheric pressure when the sample is injected and wherein the one passage is thereafter alignable with the sample passage while the other passage is aligned with the carrier passage to enable the carrier fluid to deliver the sample therein to the partition and a check valve wherein one end of the sample passage communicates via one single-passage spherical valve with the atmosphere and the other end of the sample passage is connected, via the check valve adapted to open at a predetermined pressure and close after pressure compensation and via the other single-passage spherical valve, to a gas under said predetermined pressure for dissolving the sample substance.

* * * * *